US012688920B2

(12) United States Patent
Park et al.

(10) Patent No.:  US 12,688,920 B2
(45) Date of Patent:  Jul. 21, 2026

(54) OPTIMIZATION METHOD AND SYSTEM FOR PERSONALIZED CONTRAST TEST BASED ON DEEP LEARNING

(71) Applicant: CLARIPI INC., Seoul (KR)

(72) Inventors: Hyun Sook Park, Seoul (KR); Chul Kyun Ahn, Seoul (KR); Tae Jin Kim, Seoul (KR)

(73) Assignee: CLARIPI INC., Seoul (KR)

( * ) Notice: Subject to any disclaimer, the term of this patent is extended or adjusted under 35 U.S.C. 154(b) by 433 days.

(21) Appl. No.: 18/148,286

(22) Filed: Dec. 29, 2022

(65) Prior Publication Data

US 2023/0215538 A1      Jul. 6, 2023

(30) Foreign Application Priority Data

Jan. 4, 2022    (KR) ........................ 10-2022-0001017

(51) Int. Cl.
*G16H 20/17*        (2018.01)
*G06T 7/00*         (2017.01)

(52) U.S. Cl.
CPC ........... *G16H 20/17* (2018.01); *G06T 7/0012* (2013.01); *G06T 2207/10081* (2013.01)

(58) Field of Classification Search
CPC . G06T 2207/20084; G06T 2207/20081; G06T 2207/10081; G06T 2207/10088;
(Continued)

(56) References Cited

U.S. PATENT DOCUMENTS

2015/0127376 A1*  5/2015  Ortenzi ................. A61M 5/007
                                                        705/3
2019/0313990 A1*  10/2019  Sahbaee Bagherzadeh ...............
                                                        A61B 6/583
(Continued)

FOREIGN PATENT DOCUMENTS

CN        111991020 A  * 11/2020  ............. A61B 6/481
JP        2007-7286 A      1/2007
(Continued)

OTHER PUBLICATIONS

Machine translation obtained from google patents of WO-2022163890-A1 (Year: 2022).*

(Continued)

*Primary Examiner* — Courtney Joan Nelson

(57)        ABSTRACT
Disclosed are an optimization method and system for a personalized contrast test based on deep learning, in which a contrast medium optimized for each individual patient is injected to implement optimum pharmacokinetic characteristics in a process of acquiring a medical image, the method including: obtaining drug information of a contrast medium and body information of a patient, in a contrast enhanced computed tomography (CT) scan; generating injection information of the drug to be injected into the patient by a predefined algorithm based on the drug information and the body information; injecting the drug into the patient based on the injection information, and acquiring a medical image by scanning the patient; and amplifying a contrast component in the medical image by inputting the medical image to a deep learning model trained in advance.

16 Claims, 9 Drawing Sheets

(58) Field of Classification Search

CPC ........... G06T 5/92; G06T 7/0012; G06T 5/60; G06T 5/50; G06T 2207/30004; G06T 5/94; G06T 2207/30168; G06T 11/008; G06T 11/00; G06T 2210/41; G06N 3/045; G06N 3/08; G06N 20/00; G06N 3/0464; G06N 3/0475; G16H 30/40; G16H 30/20; G16H 50/20; G16H 10/60; G16H 20/17; A61B 6/032; A61B 5/7267; A61B 6/481; A61B 6/03; A61B 6/5217; A61B 6/5211; G06V 2201/031; G06V 10/764; G06V 10/774; G06V 2201/03; G06V 10/776

See application file for complete search history.

(56) References Cited

U.S. PATENT DOCUMENTS

| | | | |
|---|---|---|---|
| 2020/0367844 A1* | 11/2020 | Dang | ........................ G06T 5/60 |
| 2021/0015438 A1 | 1/2021 | Sahbaee Bagherzadeh et al. | |

FOREIGN PATENT DOCUMENTS

| | | | | |
|---|---|---|---|---|
| JP | 2019-171055 A | 10/2019 | | |
| KR | 10-0878282 B1 | 1/2009 | | |
| KR | 10-2021-0073622 A | 6/2021 | | |
| KR | 10-2316312 B1 | 10/2021 | | |
| WO | WO-2022163890 A1 * | 8/2022 | ............. | G06N 20/00 |

OTHER PUBLICATIONS

Machine translation obtained from google patents of CN-111991020-A (Year: 2020).*

Bae, Kyongtae T., et al. "Contrast enhancement in cardiovascular MDCT: effect of body weight, height, body surface area, body mass index, and obesity." American journal of roentgenology 190.3 (2008): 777-784. (Year: 2008).*

The Extended European Search Report for European Patent Application No. 23150059.6, dated May 12, 2023.

* cited by examiner

510 generate second training image set added
with contrast component image
from first training image set ～S213 generate and train training target
deep learning model ～S214

OPTIMIZATION METHOD AND SYSTEM FOR PERSONALIZED CONTRAST TEST BASED ON DEEP LEARNING

CROSS REFERENCE TO RELATED APPLICATION

This application is based on and claims priority under 35 U.S.C. § 119 to Korean Patent Application No. 10-2022-0001017 filed on Jan. 4, 2022 in the Korean Intellectual Property Office, the disclosure of which is incorporated by reference herein in its entirety.

BACKGROUND OF THE INVENTION

Field of the Invention

The disclosure relates to an optimization method and system for a personalized contrast test based on deep learning, and more particularly to an optimization method and system for a personalized contrast test based on deep learning to acquire medical images.

Description of the Related Art

In general, medical apparatuses such as X-ray, computed tomography (CT), and magnetic resonance imaging (MRI) scanners have been used to acquire medical images. The medical images acquired through such medical apparatuses are used by a doctor as a very important basis in making a decision by determining the presence and characteristics of lesions in the procedure of diagnosing and treating a patient. In particular, contrast in a CT image acquired through the medical apparatus is very important in accurately diagnosing the lesion, and thus efforts for the contrast imaging technology to obtain high contrast in the CT image have been continued with the development of CT scanning techniques.

The conventional contrast imaging technology has already been disclosed in Korean Patent No. 10-0878282 (titled "DEVICE AND METHOD FOR DISPENSING MEDIA AS PART OF A MEDICAL PROCEDURE" and registered on Jan. 6, 2009). This registered invention is to inject a contrast medium into a patient to acquire the CT image.

Most of the conventional technologies are based on a large amount of contrast medium injected to amplify the contrast of the CT image. The contrast medium increases or decreases the permeability of a specific lesion or blood vessel in an imaging scan, and is thus useful for finding not only blood vessels and various organs but also a hidden lesion. However, the contrast medium has physical and chimeral properties distinctly different from a patient's body fluids and therefore causes problems of side effects. Accordingly, efforts to minimize the injection amount of contrast medium are needed to be accompanied in a situation where there is a lack of skills at perfectly controlling the side effects of the contrast medium.

Documents of Related Art (Patent Document) Korean Patent No. 10-0878282 (titled "DEVICE AND METHOD FOR DISPENSING MEDIA AS PART OF A MEDICAL PROCEDURE" and registered on Jan. 6, 2009)

SUMMARY OF THE INVENTION

An aspect of the disclosure is to provide an optimization method and system for a personalized contrast test based on deep learning, in which a contrast medium optimized for each individual patient is injected to implement optimum pharmacokinetic characteristics in a process of acquiring a medical image.

Another aspect of the disclosure is to provide an optimization method and system for a personalized contrast scan based on deep learning, in which a high-quality diagnostic image is acquired with the minimum injection of a contrast medium.

According to an embodiment of the disclosure, an optimization method of a personalized contrast scan based on deep learning includes: obtaining drug information of a contrast medium and body information of a patient, in a contrast enhanced computed tomography (CT) scan; generating injection information of the drug to be injected into the patient by a predefined algorithm based on the drug information and the body information; injecting the drug into the patient based on the injection information, and acquiring a medical image by scanning the patient; and amplifying a contrast component in the medical image by inputting the medical image to a deep learning model trained in advance.

The obtaining of the drug information may include: recognizing a type of drug based on at least one of text information and image information input together with the drug; and obtaining the drug information corresponding to the drug from a database.

The image information may include at least one of a barcode and a quick response (QR) code.

The obtaining of the body information may include acquiring a three-dimensional (3D) image of the patient; and obtaining, from the 3D image, at least one of volume information about the patient's body, volume information about a body region excluding a fat region, and volume information about an organ to be diagnosed.

The acquiring of the 3D image of the patient may include generating the 3D image based on a combination of two-dimensional (2D) images of the patient.

The generation of the 3D image may include combining a 2D image acquired in up and down directions of the patient and a 2D image acquired in left and right directions of the patient by two-dimensionally scanning the patient; and generating the 3D image based on the combined images.

The injecting of the drug may include injecting the drug based on the injection information through an injection device configured to inject the drug into the patient.

The injecting of the drug may include automatically adjusting at least one between an injection amount and an injection speed of the drug by the injection device.

The injecting of the drug may include outputting and providing at least between an injection amount and an injection speed of the drug to a user by the injection device.

The injection information of the drug, generated by the algorithm, may include a minimum injection amount derived in consideration of contrast amplification performed by the deep learning model.

The amplifying of the contrast component may include extracting at least one component image of contrast enhanced and unenhanced component images for the medical image by inputting the medical image of the patient to the deep learning model; and outputting a contrast amplified image for the medical image based on the medical image and the at least one extracted component image.

The optimization method of a personalized contrast scan based on deep learning may further include, before extracting the component image, extracting scan information from the medical image; and selecting at least one deep learning model corresponding to the scan information among a plurality of deep learning models trained in advance.

The extracting of the component image may include extracting at least one component image for the medical image by inputting the medical image to at least one selected deep learning model.

The method may further include, before extracting the scan information, producing at least one composite component image based on a pair of images from a first training image set; generating a second training image set based on the at least one composite component image and the first training image set; extracting the scan information from the second training image set, and grouping the second training image set into a plurality of groups based on a preset rule; and generating and training a plurality of second deep learning models to respectively correspond to the groups of the grouped second training image set.

The deep learning model selected in the selecting may include a plurality of deep learning models.

The outputting of the contrast amplified image may include multiplying the medical image and the at least one component image by preset ratios, respectively, and summing the multiplied images.

The outputting of the contrast amplified image may include multiplying the medical image and the at least one component image by preset ratios, respectively, and summing the multiplied images to generate first and second images; and outputting a composite color image by applying a preset color tone table to the first and second images.

The method may further include, before the extracting of the component image, producing at least one composite component image based on a pair of images from a first training image set; generating a second training image set based on the at least one composite component image and the first training image set; and generating and training a second deep learning model to extract at least one component image by using the second training image set.

Meanwhile, according to an embodiment of the disclosure, an optimization system of a personalized contrast scan based on deep learning includes: an input device configured to receive information about a drug; a body information generating device configured to generate body information of a patient to be injected with the drug; a drug injection information generating device configured to generate injection information of the drug to be injected into the patient by a predefined algorithm based on the drug information and the body information; an injection device configured to inject the drug into the patient based on the injection information; and an amplification device configured to amplify a contrast component in a medical image by inputting the medical image, acquired from the patient to be injected with the drug, to a deep learning model trained in advance.

The injection device may interwork with the drug injection information generating device by a wire or wirelessly, and receive the injection information from the drug injection information generating device.

According to the disclosure, the optimization method and system for the personalized contrast scan according to the disclosure have an effect on minimizing the injection amount of the contrast medium as an optimum contrast medium is injected in consideration of the contrast amplification of the medical image based on the deep learning.

Thus, the optimization method and system for the personalized contrast scan according to the disclosure have effects on fundamentally solving side effects due to the injection of the contrast medium, and making an accurate image diagnosis based on a high-quality medical image in lesion diagnosis.

The foregoing technical effects of the disclosure are not limited to the aforementioned effects, and other technical effects not mentioned above may become apparent to those skilled in the art from the following description.

DETAILED DESCRIPTION OF THE INVENTION

Hereinafter, embodiments of the disclosure will be described in detail with reference to the accompanying drawings. However, the disclosure is not limited to the embodiments set forth herein, but may be implemented in various forms. The following embodiments are merely provided to make the disclosure complete, and to make a person having ordinary knowledge in the art fully understand the scope of the disclosure. In the accompanying drawings, the shapes and the like of elements may be exaggerated for clarity, and like numerals denote like elements.

Figure 1:
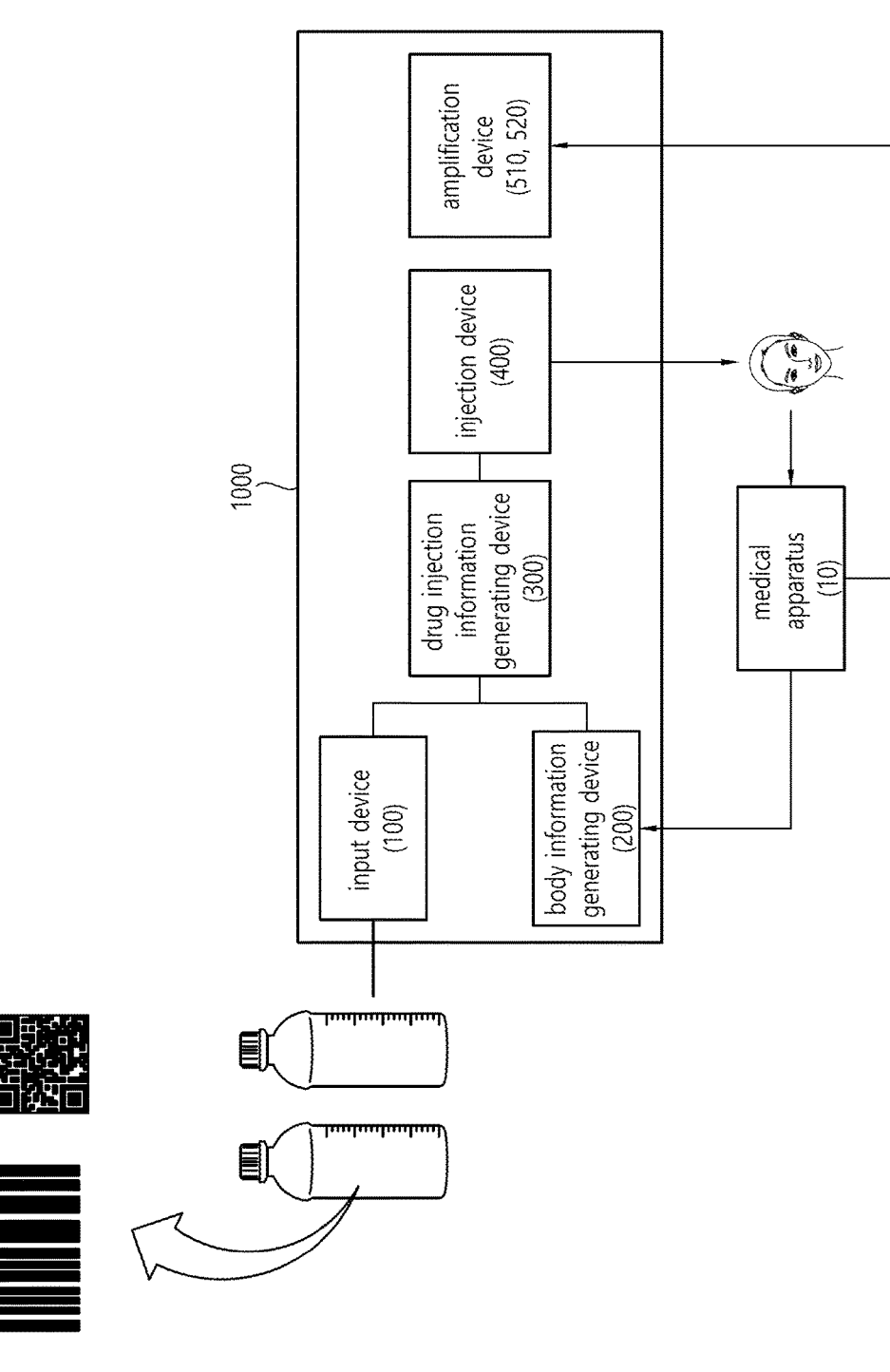
FIG. 1 is a conceptual view schematically showing an optimization system for a personalized contrast scan based on deep learning according to an embodiment of the disclosure.

FIG. 1 is a conceptual view schematically showing an optimization system for a personalized contrast scan based on deep learning according to an embodiment of the disclosure.

As shown in FIG. 1, an optimization system 1000 for the personalized contrast scan based on the deep learning according to an embodiment of the disclosure (hereinafter referred to as an optimization system) acquires a medical image by deriving an optimized dosage form of a drug such as a contrast medium in a process of acquiring the medical image, and generates a readout image by amplifying the contrast of the acquired medical image.

Here, a medical apparatus 10 may include a computed tomography (CT) scanner, a magnetic resonance imaging (MRI) scanner, a position emission tomography (PET) scanner, etc., and a medical image may include a CT image. However, there are no limits to the types of medical apparatuses 10 and the formats of medical images.

Such an optimization system 1000 may include an input device 100, a body information generating device 200, a drug injection information generating device 300, an injection device 400, and an amplification device 510, 520. However, the optimization system 1000 is not limited to an individual configuration, but connected to a computer system or the like single or multiple processors so that a series of processes thereof can be performed in the computer system or the like single or multiple processors.

Meanwhile, the input device 100 acquires information about a drug. For example, the input device 100 may recognize the type of drug by acquiring text or image information written on a bottle, a cover, or the like in which the drug is accommodated. In this case, the input device 100 may photograph or recognize a barcode or a quick response (QR) code written on the bottle or the cover.

Further, the body information generating device 200 generates body information of a patient to be injected with the drug. In this case, the body information generating device 200 generates the body information based on a three-dimensional (3D) image obtained by scanning the patient to generate his/her body information.

For example, in the case of a patient who has already been scanned, the body information generating device 200 may obtain the body information by calling the patient's 3D image stored in a database.

On the other hand, in the case of a new patient, the body information generating device 200 may receive a new 3D image acquired through 3D scanning performed in the medical apparatus 10. Further, in the case of a new patient, a summary 3D image may be generated by performing not a 3D scan but a 2D preliminary scan to reduce a radiation dose. In this case, the body information generating device 200 may generate the summary 3D image based on 2D images acquired in up and down directions of the patient and 2D images acquired in left and right directions of the patient. Here, the generation of the summary 3D image based on the 2D images may be performed by a deep learning model trained in advance, but not limited thereto.

Meanwhile, the body information generating device 200 generates the body information based on the provided 3D image.

For example, the body information generating device 200 may obtain information about the volume of a patient's whole body through the 3D image. In addition, the body information generating device 200 may obtain volume information excluding fat from the patient's whole body. Because the fat is not activated even when injected with the contrast medium or the like drug, the body information generating device 200 may obtain the volume information excluding the volume of fat from the volume of the patient's whole body in order to prevent the unnecessary injection of the drug. Further, the body information generating device 200 may obtain information about the volume of an organ, of which a lesion will be diagnosed, in the volume of the patient's whole body.

Meanwhile, the drug injection information generating device 300 generates injection information about a drug to be injected into a patient based on the information about the drug provided from the input device 100, and the body information provided from the body information generating device 200. The drug injection information may include the concentration, injection amount, injection speed, etc., of a drug and a saline solution, which are merely for an embodiment of the disclosure, and do not limit the drug injection information.

For example, the drug injection information generating device 300 may generate the drug injection information based on the deep learning model trained in advance. Here, the deep learning model uses drug information and body information as input data to generate the drug injection information as a learning result of the deep learning model. In this case, the deep learning model may generate the drug injection information in consideration of contrast amplification (to be described later). In other words, the optimization system 1000 according to the disclosure amplifies a contrast component by applying secondary processing to the medical image acquired by injecting the drug into a patient. Thus, the drug injection amount included in the drug injection information is not a drug injection amount for acquiring an optimum medical image but the minimum drug injection amount considering the amplification of the contrast component.

Meanwhile, the injection device 400 interworks with the drug injection information generating device 300 by a wire or wirelessly. The injection device 400 refers to a device for injecting a drug into a patient actually, and is configured to administer various drugs such as the contrast medium and the saline solution to a patient. The injection device 400 obtains the drug injection information personalized to a patient from the drug injection information generating device 300, so that the drug can be injected into a patient based on the obtained information.

For example, the injection device 400 may inject the drug personalized to each individual patient while automatically adjusting the injection amount, injection speed, etc., of the drug based on the information included in the drug injection information. In other words, the injection device 400 may automatically inject the drug based on the set drug injection information without involvement of a person concerned.

For example, the injection device 400 may include a display panel configured to output the drug injection information. Thus, the person concerned can inject the drug personalized to each individual patient by adjusting the injection amount, injection speed, etc., of the drug while referring to the drug injection information output through the display panel.

Then, the patient injected with the drug may undergo the scan through the medical apparatus 100. In addition, the medical apparatus 100 acquires the medical image including the contrast component.

Meanwhile, when the medical image including the contrast component is acquired, the amplification device 510, 520 amplifies the contrast of the medical image to generate the readout image.

Figure 2:
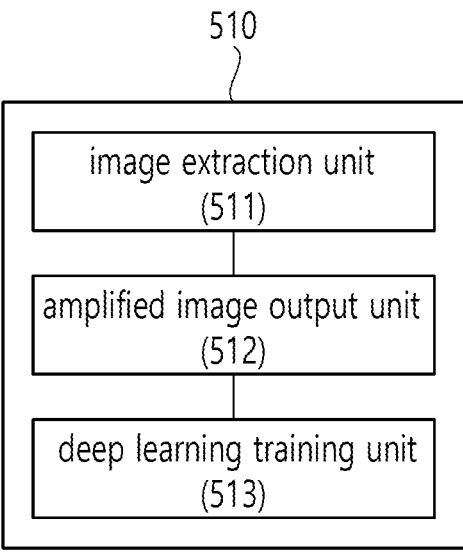
FIG. 2 is a block diagram showing a schematic configuration of an amplification device according to an embodiment in an optimization system for a personalized contrast scan based on deep learning according to the disclosure.

FIG. 2 is a block diagram showing a schematic configuration of an amplification device according to an embodiment in an optimization system for a personalized contrast scan based on deep learning according to the disclosure.

As shown in FIG. 2, the amplification device 510 according to an embodiment may include an image extraction unit 511, an amplified image output unit 512, and a deep learning training unit 513.

The image extraction unit 511 may input the medical image including the contrast component to the deep learning model trained in advance, and extract at least one component image of contract enhanced and unenhanced component images as a learning result of the deep learning model.

Further, the amplified image output unit 512 may output the contrast amplified image based on the extracted component image.

For example, the amplified image output unit 512 may multiply the component image extracted by the image extraction unit 511 and the medical image including the contrast component by respectively set ratios, and sum the multiplied images, thereby outputting a contrast amplified medical image for the medical image including the contrast component.

For example, the amplified image output unit 512 may multiply the component image extracted from the image extraction unit 511 and the medical image including the contrast component by respectively set ratios, sum the multiplied images to generate a first image and a second image, and apply a preset color tone table to each of the first and the second image, thereby outputting a composite color image.

The deep learning training unit 513 may generate and train a training target deep learning model. The deep learning training unit 513 may generate and train the training target deep learning model before the image extraction unit 511 extracts the component image from the medical image including the contrast component.

For example, the deep learning training unit 513 may train the training target deep learning model based on a training image set, before the image extraction unit 511 extracts at least one component image from the medical image including the contrast component.

In addition, the deep learning training unit 513 may combine a pair of images from a first training image set into at least one composite component image before training the training target deep learning model. Further, the deep learning training unit 513 may generate a second training image set based on at least one composite component image and the original image of the first training image set. Further, the deep learning training unit 513 may train the training target deep learning model based on the generated second training image set.

Here, the original image of the first training image set may include a pair of images, such as an image scanned before injecting the drug and an image scanned after injecting the drug. In this case, the deep learning training unit 513 may produce a contrast enhanced composite component image made up of the pair of images acquired before and after injecting the drug.

For example, the deep learning training unit 513 may produce the contrast enhanced component image by subtracting the image before injecting the drug from the image after injecting the drug. In this case, the deep learning training unit 513 may use the image before injecting the drug as the contrast unenhanced component image.

Further, the deep learning training unit 513 may apply a movement compensation computation based on a preset reference to the image before injecting the contrast medium and the image after injecting the contrast medium.

In addition, the original image of the first training image set may include a pair of low and high energy images scanned after injecting the drug through the medical apparatus having a dual energy scanning function. In this case, the deep learning training unit 513 may produce a contrast enhanced composite component image based on the pair of low and high energy images.

Further, the deep learning training unit 513 may multiply each of the low energy image and the high energy image by a preset ratio and sum the multiplied images, thereby producing a contrast enhanced composite component image.

Further, the deep learning training unit 513 may multiply each of the low energy image and the high energy image by another preset ratio and sum the multiplied images, thereby producing a contrast unenhanced composite component image.

Further, the deep learning training unit 513 produces a contrast enhanced composite component image and a contrast unenhanced composite component image based on the pair of images from the first training image set. Then, the contrast enhanced composite component image is multiplied by at least one preset ratio. Then, the multiplied contrast enhanced composite component image is added to the contrast unenhanced composite component image, thereby producing at least one low contrast composite image.

In this way, the deep learning training unit 513 may generate the second training image set including at least one component image among the at least one low contrast composite image, the contrast enhanced composite component image, and the contrast unenhanced composite component image based on the pair of images from the first training image set.

Further, the deep learning training unit 513 may generate the training target deep learning model before the image extraction unit 511 extracts at least one component image from the medical image including the contrast component. Further, the deep learning training unit 513 may generate the second training image set, to which at least one composite component image and at least one low contrast composite image based on the pair of images from the first training image set, so that the training target deep learning model can have a function of extracting at least one component image from an input contrast enhanced image received therein.

Further, the deep learning training unit 513 may input the low contrast composite image for every image from the second training image set to the training target deep learning model, and repetitively train the training target deep learning model to have a minimum difference between the at least one composite component image and the output of the training target deep learning model.

Figure 3:
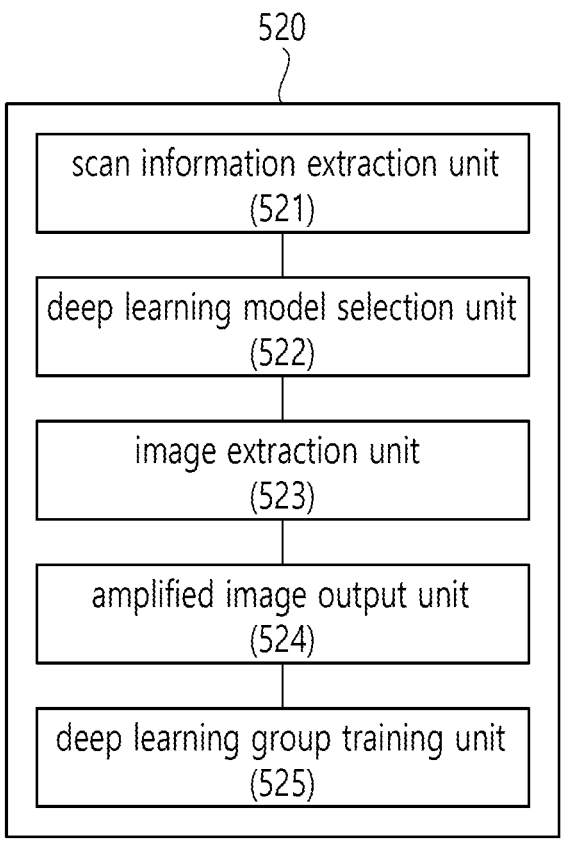
FIG. 3 is a block diagram showing a schematic configuration of an amplification device according to an alternative embodiment in an optimization system for a personalized contrast scan based on deep learning according to the disclosure.

FIG. 3 is a block diagram showing a schematic configuration of an amplification device according to an alternative embodiment in an optimization system for a personalized contrast scan based on deep learning according to the disclosure.

An image extraction unit 523 and an amplified image output unit 524 of the amplification device 520 described below with reference to FIG. 3 may be the same as or correspond to the image extraction unit 511 and the amplified image output unit 512 of the amplification device 510 described above with reference to FIG. 2. Although omitted below, the description of the image extraction unit 523 and the amplified image output unit 524 may be replaced by the description of the image extraction unit 511 and the amplified image output unit 512.

As shown in FIG. 3, the amplification device 520 according to the alternative embodiment may include a scan information extraction unit 521, a deep learning model selection unit 522, the image extraction unit 523, the amplified image output unit 524, and a deep learning group training unit 525.

The scan information extraction unit 521 may extract scan information from an input medical image including a contrast component. The scan information may include scan part information and scan attribute information of an image.

For example, the scan part information may refer to information about organs. In other words, the scan part information means information about a region of interest in human organs, such as a head, a chest, and an abdomen.

For example, the scan attribute information refers to information about scan variables which affect metal artifact characteristics in a medical image, and may for instance mean information about reconstruction kernel, tub voltage, tube current, slice thickness, etc.

The scan information extraction unit 521 may extract the scan information from the medical image including the contrast component. For example, the scan information extraction unit 521 may extract the scan information from header information included in the medical image including the contrast component. Further, the scan information extraction unit 521 may extract the scan information by inputting the medical image including the contrast component to a predefined classifier. In this case, the predefined classifier may be configured to extract one or more image characteristics from the medical image including the contrast component, and assign the extracted image characteristics to one of a predefined number of categories.

Meanwhile, the deep learning model selection unit 522 may select at least one deep learning model, which corresponds to the scan information extracted by the scan information extraction unit 521, among the deep learning models trained in advance.

Further, the deep learning model selection unit 522 may apply a preset rule to the scan information extracted by the scan information extraction unit 521, thereby selecting at least one deep learning model, which corresponds to the scan information extracted by the scan information extraction unit 521, among the plurality of deep learning models trained in advance.

Meanwhile, the image extraction unit 523 may extract at least one component image based on at least one deep learning model selected by the deep learning model selection unit 522.

In addition, the amplified image output unit 524 may output the contrast amplified image based on at least one extracted component image and the medical image including the contrast component.

In this way, the amplification device 520 may include a plurality of deep learning models. Here, the plurality of deep learning models may refer to the deep learning models trained in advance by the deep learning group training unit 525 (to be described later), and may mean the deep learning models trained in advance to output at least one component image with respect to the medical image, which includes the contrast component and is input to each of the deep learning models.

The plurality of deep learning models taken into account by the amplification device 520 may be generated by the deep learning group training unit 525. The deep learning group training unit 525 may generate the plurality of deep learning models based on the scan information. In other words, the deep learning group training unit 525 may generate and train a plurality of training target deep learning models. In particular, the deep learning group training unit 525 may generate a plurality of deep learning models based on a combination of the scan part information and the scan attribute information of the image included in the scan information.

Thus, the amplification device 520 may include the plurality of deep learning models generated based on the scan information. The plurality of deep learning models generated based on a combination of the scan part information and the scan attribute information may be respectively trained by the deep learning group training unit 525 through the training image sets grouped according to combinations of the scan part information and the scan attribute information.

As an example, the deep learning model selection unit 522 may select at least one deep learning model corresponding to the scan information extracted by the scan information extraction unit 521 among the plurality of deep learning models generated based on the scan information and trained in advance.

As an example, it is assumed that the medical image including the contrast component is an image of a first scan part, e.g., an abdomen, i.e., an abdominal scan image, reconstructed with first scan attributes such as a low dose and a thick slice. In this case, the deep learning model selection unit 522 may select a single deep learning model trained with a training image corresponding to the scan part of the abdomen and having the scan attributes such as the low dose and the thick slice as the deep learning model corresponding to the first scan part and having the first scan attributes among the plurality of deep learning models trained in advance.

As another example, it is assumed that the medical image including the contrast component is an image of the first scan part, e.g., the abdomen, i.e., the abdominal scan image, reconstructed with second scan attributes such as an ultralow dose and a thin slice. In this case, the deep learning model selection unit 522 may select a single deep learning model trained with a training image corresponding to the scan part of the abdomen and having the scan attributes such as the ultralow dose and the thin slice as the deep learning model corresponding to the first scan part and having the second scan attributes among the plurality of deep learning models trained in advance.

As still another example, it is assumed that the medical image including the contrast component is an image of a second scan part, e.g., a chest, i.e., a chest scan image, reconstructed by applying third scan attributes to a first region, e.g., applying a reconstruction kernel of a high sharpness as a first sharpness to a lung region, and by applying fourth scan attributes to a second region, e.g., applying a reconstruction kernel of a low sharpness as a second sharpness to a soft tissue region. In this case, the deep learning model selection unit 522 may select a deep learning model corresponding to the third scan attributes and a deep learning model corresponding to the second scan part among the plurality of deep learning models trained in advance. Specifically, the deep learning model selection unit 522 may select two deep learning models, which include the deep learning model trained with a training image corresponding to the scan part of the chest and having the reconstruction kernel of the high sharpness, and the deep learning model trained with a training image corresponding to the scan part of the chest and having the reconstruction kernel of the low sharpness, among the plurality of deep learning models trained in advance.

In this way, the deep learning model selection unit 522 may select one or a plurality of deep learning models among the plurality of deep learning models trained in advance, in consideration of a combination of the scan part information and the scan attribute information included in the extracted scan information based on the scan information extracted by the scan information extraction unit 521.

The amplified image output unit 524 inputs the medical image including the contrast component to at least one deep learning model selected by the deep learning model selection unit 522, so that the at least one selected deep learning model can extract at least one component image from the medical image including the contrast component. In addition, the amplified image output unit 524 multiplies the at least one extracted component image and the medical image including the contrast component by preset ratios, respectively, and sums the multiplied images to produce an image, thereby outputting the contrast amplified medical image.

For example, it is assumed that the deep learning model selected by the deep learning model selection unit 522 is a single deep learning model. In this case, the amplified image output unit inputs the medical image including the contrast component to the single deep learning model selected by the deep learning model selection unit 522 so that the single deep learning model can extract at least one component image from the medical image including the contrast component, and then multiplies the at least one extracted component image and the medical image including the contrast component by preset ratios, respectively, and sums the multiplied images to produce an image, thereby outputting the contrast amplified medical image.

For example, it is assumed that the deep learning model selected by the deep learning model selection unit 522 is the plurality of deep learning models. In this case, the amplified image output unit 524 inputs the medical image including the contrast component to each of the plurality of deep learning models selected by the deep learning model selection unit 522 so that the plurality of deep learning models can respectively extract the contrast enhanced component images from the input medical image including the contrast component. In addition, the amplified image output unit 524 multiplies the at least one extracted component image and the medical image including the contrast component by preset ratios, respectively, and sums the multiplied images to produce an image, thereby outputting the contrast amplified medical image.

In this case, the amplified image output unit 524 may multiply the medical image including the contrast component and at least one component image by respectively set ratios, sum the multiplied images to produce a first image and a second image, and apply a preset color tone table to each of the first and second images, thereby outputting a composite color image.

The deep learning group training unit 525 may generate and train a plurality of training target deep learning models before the scan information extraction unit 521 extracts the scan information from the medical image including the contrast component.

In this case, the deep learning group training unit 525 may produce at least one low contrast composite image and at least one composite component image based on the pair of images from the first training image set, and use the produced composite images to generate the second training image set. Further, the deep learning group training unit 525 may extract the scan information from the second training image set, and group the second training image set into a plurality of groups based on a preset rule. Further, the deep learning group training unit 525 may generate and train a plurality of training target deep learning models to correspond to the groups of second training image set, respectively. The deep learning group training unit 525 may train each of the plurality of generated training target deep learning models.

In this case, the plurality of training target deep learning models trained by the deep learning group training unit 525 may refer to a plurality of deep learning models trained in advance and considered in the deep learning model selection unit 522.

In this way, when the medical image including the contrast component is given as an input, the deep learning group training unit 525 may train each of the plurality of training target deep learning models generated according to the scan attributes so that the deep learning model corresponding to the scan attributes of the medical image including the contrast component can output at least one component image by taking the medical image including the contrast component as the input.

In this way, when the medical image including the contrast component is given in the amplification device 520 according to the alternative embodiment, the deep learning model selection unit 522 may select a deep learning model corresponding to the scan attributes of the medical image including the contrast component so that the deep learning model can operate corresponding to the scan attributes of the medical image including the contrast component among the plurality of deep learning models trained in advance. Then, the amplified image output unit 524 may output the medical image of which the contrast is amplified by the selected deep learning model.

The amplification device 520 may train each of the plurality of deep learning models through the deep learning group training unit 525 so that each of the plurality of deep learning models can output a high contrast image by amplifying the contrast of the medical image including the contrast component input to each deep learning model. In this way, the amplification device 520 may select the deep learning model corresponding to the scan information extracted from the medical image including the contrast component based on the plurality of deep learning models trained in advance. Then, the amplification device 520 may provide the medical image including the contrast component as an input to the selected deep learning model, and thus output the contrast amplified medical image for the medical image including the contrast component from the selected deep learning model.

Meanwhile, the amplification device 520 may output a high contrast medical image from an input of a low-contrast image, e.g., a low-concentration drug injection image, based on the plurality of deep learning models trained in advance. Further, the amplification device 520 provides a method of training the deep learning model to output a high contrast medical image from a low contrast image, and the quality of the contrast amplified medical image output through such a trained deep learning model may be high.

Further, the amplification device 520 may train the training target deep learning model with the training image set, and thus output a medical image of which the contrast is more effectively amplified from a low contrast image (i.e., the medical image including the contrast component) acquired by scanning after actually injecting a low concentration drug.

Meanwhile, the operations of the optimization system for the personalized contrast scan according to an embodiment will be described below with reference to the accompanying drawings. However, the foregoing elements will be given the same reference numerals, but repetitive descriptions thereof will be avoided.

Figure 4:
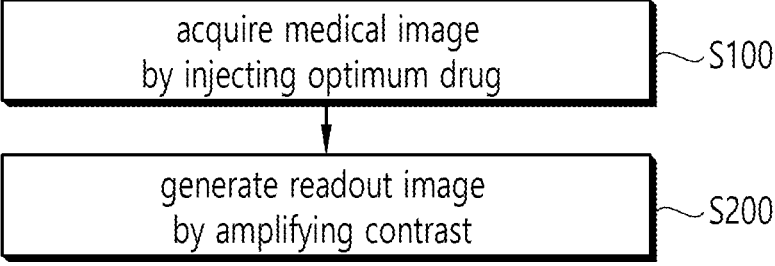
FIG. 4 is a flowchart showing an optimization method of a personalized contrast scan based on deep learning according to an embodiment of the disclosure.

FIG. 4 is a flowchart showing an optimization method of a personalized contrast scan based on deep learning according to an embodiment of the disclosure.

As shown in FIG. 4, the optimization method of the personalized contrast scan based on the deep learning according to an embodiment acquires a medical image by deriving an optimized dosage form of a drug such as a contrast medium in the process of acquiring the medical image (S100), and generates a readout image by amplifying the contrast of the acquired medical image (S200).

Below, the process S100 of acquiring the medical image, and the process S200 of generating the readout image by amplifying the contrast will be described separately.

Figure 5:
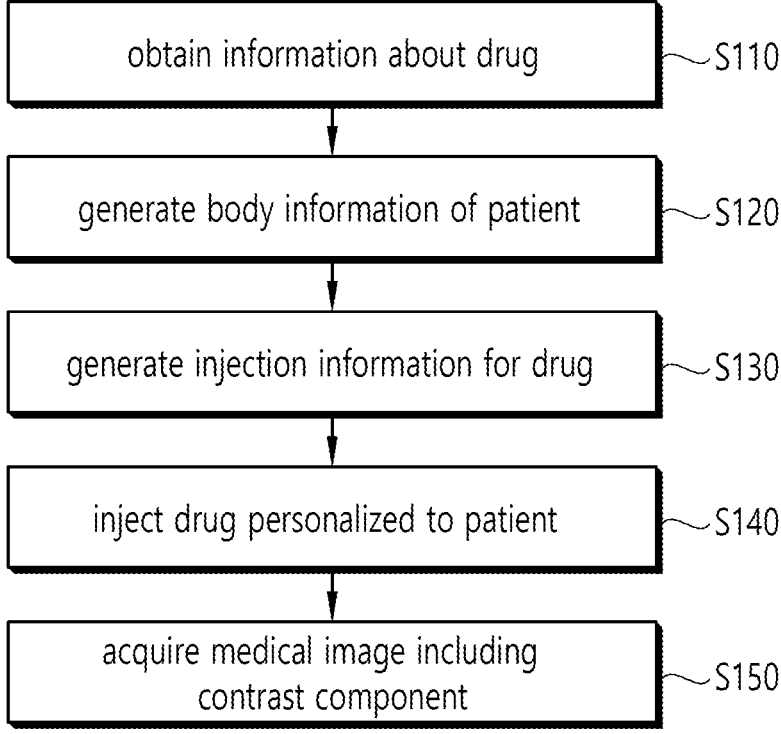
FIG. 5 is a flowchart showing a process of acquiring a medical image in an optimization method of a personalized contrast scan based on deep learning according to an embodiment of the disclosure.

FIG. 5 is a flowchart showing a process of acquiring a medical image in an optimization method of a personalized contrast scan based on deep learning according to an embodiment of the disclosure.

As shown in FIG. 5, the input device 100 according to an embodiment obtains information about a drug (S110).

For example, the input device 100 may photograph or recognize a barcode or a QR code written on a bottle or a cover, and thus the drug injection information generating device 300 may call the corresponding information about the drug from a database.

Then, the body information generating device 200 generates body information of a patient to be injected with the drug (S120). In this case, the body information generating device 200 acquires 3D image, and generates the body information, which includes information about the volume of the patient's whole body, volume information excluding the volume of fat, and information about the volume of an organ, from the 3D image.

In addition, the drug injection information generating device 300 generates injection information about the drug to be injected into the patient, based on the body information provided from the body information generating device 200 and the drug information obtained by the input device 100 (S130). In this case, the drug injection information generating device 300 generates the drug injection information based on the deep learning model, and the deep learning model in this case may generate the drug injection information in consideration of the contrast amplification. In other words, the deep learning model may generate the drug injection information including the minimum drug injection amount considering the amplification of the contrast component.

Then, the injection device 400 obtains the drug injection information personalized to the patient from the drug injection information generating device 300, and injects the drug into the patient based on the obtained information (S140).

Further, the patient injected with the drug may be scanned through the medical apparatus 10. In addition, the medical apparatus 10 acquires the medical image including the contrast component (S150).

Meanwhile, when the medical image including the contrast component is acquired, a readout image is generated by amplifying the contrast of the medical image.

First, a method of generating the readout image based on the amplification device according to the embodiment shown in FIG. 2 will be described.

Figure 6:
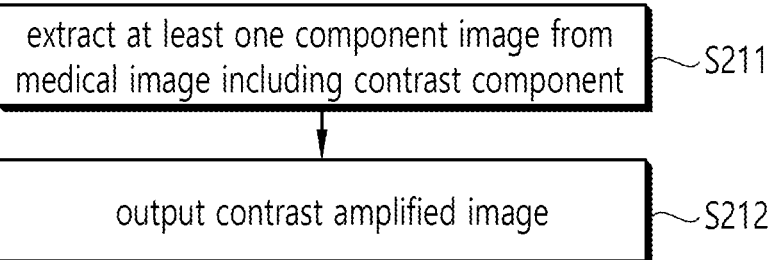
FIG. 6 is a flowchart showing a method of amplifying contrast based on an amplification device according to an embodiment in an optimization method of a personalized contrast scan based on deep learning according to the disclosure.
Figure 7:
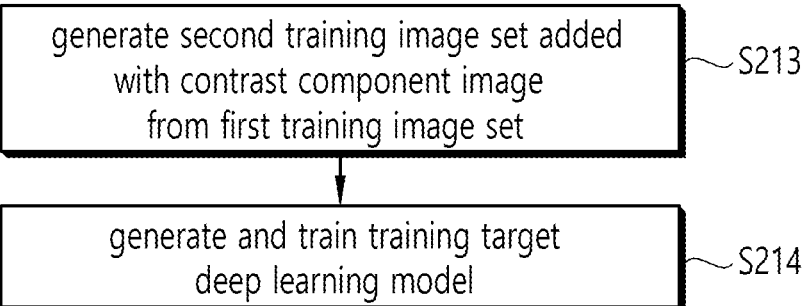
FIG. 7 is a flowchart showing a method of training a deep learning model for an amplification device according to an embodiment in an optimization method of a personalized contrast scan based on deep learning according to the disclosure.

FIG. 6 is a flowchart showing a method of amplifying contrast based on an amplification device according to an embodiment in an optimization method of a personalized contrast scan based on deep learning according to the disclosure, and FIG. 7 is a flowchart showing a method of training a deep learning model for an amplification device according to an embodiment in an optimization method of a personalized contrast scan based on deep learning according to the disclosure.

As shown in FIGS. 6 and 7, the image extraction unit 511 according to an embodiment may extract at least one component image of contrast enhanced and unenhanced component images by taking the medical image including the contrast component as an input to the previously trained model (S211).

Then, the amplified image output unit 512 may output the contrast amplified medical image for the medical image including the contrast component based on at least one component image and the medical image including the contrast component (S212).

In this case, the amplified image output unit 512 may multiply the at least one extracted component image and the medical image including the contrast component by preset ratios, respectively, and sum the multiplied images, thereby outputting the contrast amplified medical image for the medical image including the contrast component.

For example, the amplified image output unit 512 may multiply the at least one extracted component image and the medical image including the contrast component by preset ratios, respectively, sum the multiplied images to generate a first image and a second image, and apply a preset color tone table to each of the first and second images, thereby outputting a composite color image.

Meanwhile, as the amplification method, the training target deep learning model may be generated and trained before extracting the component image.

The training of the deep learning model is performed before extracting at least one component image from the medical image including the contrast component. The training of the deep learning model may generate the second image set, which includes at least one component image among at least one low contrast composite image, a contrast enhanced composite component image, and a contrast unenhanced composite component image, based on the pair of images from the first training image set, in order to train the deep learning model included in the amplification device 510 (S213).

In this case, the deep learning training unit 513 may produce the contrast enhanced composite component image and the contrast unenhanced composite component image based on a pair of original images from the first training image set, and produce at least one low contrast composite image based on the produced composite component images.

In this case, the deep learning training unit 513 may multiply the contrast enhanced composite component image by at least one preset ratio, and add the multiplied image to the contrast unenhanced composite component image, thereby producing at least one low contrast composite image.

Here, the second training image set may include a pair of at least one composite component image and at least one low contrast composite image produced based on the original image from the second training image set.

The deep learning training unit 513 may train the training target deep learning model based on the pair of at least one composite component image and at least one low contrast composite image acquired by applying the original image of the first training image set to the image extraction unit (S214).

Further, the deep learning training unit 513 may input the low contrast composite image for every image from the second training image set to the training target deep learning model, so that the training target deep learning model can have a function of extracting at least one component image from the input medical image including the contrast component received therein. In addition, the deep learning training unit 513 may repetitively train the training target deep learning model to have a minimum difference between the at least one composite component image and the output of the training target deep learning model.

Meanwhile, a method of generating the readout image based on the amplification device 520 according to the alternative embodiment of FIG. 3 will be described below.

Figure 8:
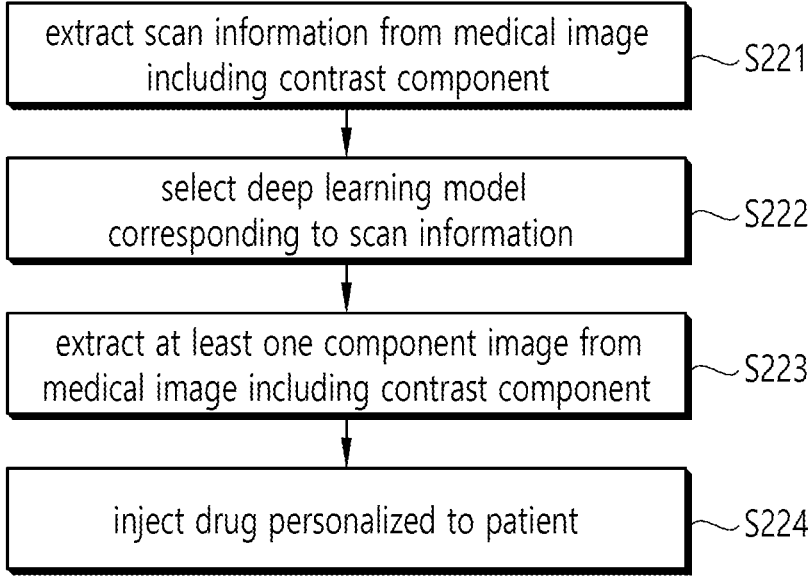
FIG. 8 is a flowchart showing a method of amplifying contrast based on an amplification device according to an alternative embodiment in an optimization method of a personalized contrast scan based on deep learning according to the disclosure.
Figure 9:
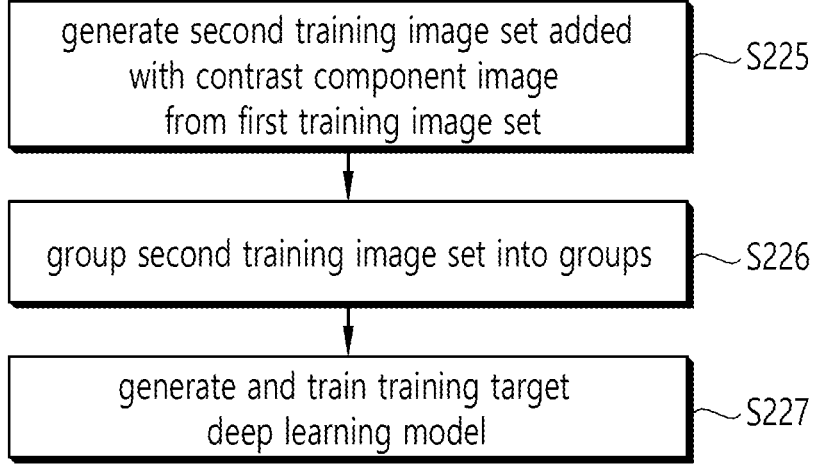
FIG. 9 is a flowchart of showing a method of training a deep learning model for an amplification device according to an embodiment in an optimization method of a personalized contrast scan based on deep learning according to the disclosure.

FIG. 8 is a flowchart showing a method of amplifying contrast based on an amplification device according to an alternative embodiment in an optimization method of a personalized contrast scan based on deep learning according to the disclosure, and FIG. 9 is a flowchart of showing a method of training a deep learning model for an amplification device according to an embodiment in an optimization method of a personalized contrast scan based on deep learning according to the disclosure.

As shown in FIGS. 8 and 9, the scan information extraction unit 521 according to an embodiment may extract the scan information from the medical image including the contrast component (S221).

Then, the deep learning model selection unit 522 may select at least one deep learning model corresponding to the extracted scan information among the plurality of deep learning models trained in advance (S222).

In addition, the image extraction unit 523 may extract at least one component image for the medical image including the contrast component by taking the medical image including the contrast component as an input to the at least one selected deep learning model (S223).

Then, the amplified image output unit 524 may output the contrast amplified medical image for the medical image including the contrast component (S224).

Meanwhile, as the amplification method, the training target deep learning model may be generated and trained before extracting the component image.

The deep learning group training unit 525 produces at least one composite component image and at least one low contrast composite image based on the first training image set so as to train the deep learning models before the scan information extraction unit 521 extracts the scan information from the medical image including the contrast component. In addition, the deep learning group training unit 525 may use the produced images to generate the second training image set (S225).

The deep learning group training unit 525 may use the pair of at least one low contrast composite image and at least one composite component image to train the training target deep learning.

In addition, the deep learning group training unit 525 may extract the scan information from the second training image set, and group the second training image set into a plurality of groups based on a preset rule (S226).

In this case, the deep learning group training unit 525 may group the second image set into a plurality of groups, thereby generating a training image set according to scan parts and scan attributes.

In addition, the deep learning group training unit 525 may generate a plurality of training target deep learning models to correspond to the plurality of generated groups of the second training image set, and train the generated training target deep learning models. In other words, the deep learning group training unit 525 may generate and train the plurality of training target deep learning models corresponding to the groups of the grouped second training image sets (S227).

Specifically, the deep learning group training unit 525 may generate and train the training target deep learning model for each scan part corresponding to each training image set generated for each scan part. Further, the deep learning group training unit 525 generate and train the training target deep learning model for each scan attribute corresponding to each training image set generated for each scan attribute.

The deep learning group training unit 525 may use the plurality of generated training image sets, i.e., the plurality of grouped training image sets to train the plurality of training target deep learning models.

For example, the deep learning group training unit 525 may use the training image sets generated for each scan part and each scan attribute to train the deep learning models generated corresponding to the training image sets and trained according to scan parts and scan attributes.

Further, the deep learning group training unit 525 makes each of the plurality of training target deep learning models have a function of extracting at least one component image from the input medical image including the contrast component received therein. To this end, the deep learning group training unit 525 may transmit the low contrast composite image for every image from the groups of the grouped second training image sets as an input to the training target deep learning model, and repetitively train the training target deep learning model to have a minimum difference between the at least one composite component image and the output of the training target deep learning model.

For example, the deep learning group training unit 525 may use the training image set generated for each scan part, thereby repetitively training the training target deep learning models generated according to the scan parts.

For example, the deep learning group training unit 525 may use the training image set generated for each scan attribute, thereby repetitively training the training target deep learning models generated according to the scan attributes.

In this way, the optimization method and system for the personalized contrast scan according to the disclosure have an effect on minimizing the injection amount of the contrast medium as an optimum contrast medium is injected in consideration of the contrast amplification of the medical image based on the deep learning.

Thus, the optimization method and system for the personalized contrast scan according to the disclosure have effects on fundamentally solving side effects due to the injection of the contrast medium, and making an accurate image diagnosis based on a high-quality medical image in lesion diagnosis.

The embodiments of the disclosure described above and illustrated in the accompanying drawings should not be construed as limiting the technical spirit of the disclosure. The scope of disclosure should be limited only by the matters disclosed in the appended claims, and various modifications and changes can be made thereto by a person having ordinary knowledge in the art to which the disclosure pertains. Accordingly, such various modifications and changes would fall into the scope of the disclosure as long as they are apparent to a person having ordinary knowledge in the art.

What is claimed is:

1. An optimization method of a personalized contrast scan based on deep learning, the method comprising:

obtaining drug information of a contrast medium and body information of a patient, in a contrast enhanced computed tomography (CT) scan;

generating injection information of the drug to be injected into the patient by a predefined algorithm based on the drug information and the body information;

injecting the drug into the patient based on the injection information, and acquiring a medical image by scanning the patient; and amplifying a contrast component in the medical image by inputting the medical image to a deep learning model trained in advance, wherein the injection information of the drug, generated by the algorithm, comprises a minimum injection amount that is calculated by: 1) predicting an image contrast enhancement output of the deep learning model prior to acquiring the medical image, and 2) optimizing the injection amount to be sufficient for the deep learning model to generate an image from which a diagnosis can be made after contrast amplification, wherein obtaining the body information comprises:

acquiring a three-dimensional (3D) image of the patient; and obtaining, from the 3D image, volume information about a body region excluding a fat region.

2. The method of claim 1, wherein the obtaining of the drug information comprises:

recognizing a type of drug based on text information or image information input together with the drug; and obtaining the drug information corresponding to the drug from a database.

3. The method of claim 2, wherein the image information comprises a barcode or a quick response (QR) code.

4. The method of claim 1, wherein the acquiring of the 3D image of the patient comprises generating the 3D image based on a combination of two-dimensional (2D) images of the patient.

5. The method of claim 4, wherein the generation of the 3D image comprises:

combining a 2D image acquired in up and down directions of the patient and a 2D image acquired in left and right directions of the patient by two-dimensionally scanning the patient; and generating the 3D image based on the combined images.

6. The method of claim 1, wherein the injecting of the drug comprises injecting the drug based on the injection information.

7. The method of claim 6, wherein the injecting of the drug comprises automatically adjusting one or both of an injection amount and an injection speed of the drug.

8. The method of claim 6, wherein the injecting of the drug comprises outputting and providing one or both of an injection amount and an injection speed of the drug to a user.

9. The method of claim 1, wherein the amplifying of the contrast component comprises:

extracting at least one component image of contrast enhanced and unenhanced component images for the medical image by inputting the medical image of the patient to the deep learning model; and outputting a contrast amplified image for the medical image based on the medical image and the at least one extracted component image.

10. The method of claim 9, further comprising: before extracting the component image, extracting scan information from the medical image; and selecting at least one deep learning model corresponding to the scan information among a plurality of deep learning models trained in advance.

11. The method of claim 10, wherein the extracting of the component image comprises extracting at least one component image for the medical image by inputting the medical image to at least one selected deep learning model.

12. The method of claim 10, further comprising: before extracting the scan information, producing at least one composite component image based on a pair of images from a first training image set;

generating a second training image set based on the at least one composite component image and the first training image set;

extracting the scan information from the second training image set, and grouping the second training image set into a plurality of groups based on a preset rule; and generating and training a plurality of second deep learning models to respectively correspond to the groups of the grouped second training image set.

13. The method of claim 12, wherein the deep learning model selected in the selecting comprises a plurality of deep learning models.

14. The method of claim 9, wherein the outputting of the contrast amplified image comprises multiplying the medical image and the at least one component image by preset ratios, respectively, and summing the multiplied images.

15. The method of claim 9, wherein the outputting of the contrast amplified image comprises:

multiplying the medical image and the at least one component image by preset ratios, respectively, and summing the multiplied images to generate first and second images; and outputting a composite color image by applying a preset color tone table to the first and second images.

16. The method of claim 9, further comprising: before the extracting of the component image, producing at least one composite component image based on a pair of images from a first training image set;

generating a second training image set based on the at least one composite component image and the first training image set; and generating and training a second deep learning model to extract at least one component image by using the second training image set.

* * * * *